US010335525B2

(12) United States Patent
Felber et al.

(10) Patent No.: US 10,335,525 B2
(45) Date of Patent: Jul. 2, 2019

(54) BREASTSHIELD WITH MEDIA SEPARATION

(71) Applicant: MEDELA HOLDING AG, Baar (CH)

(72) Inventors: Armin Felber, Lucerne (CH); Etienne Furrer, Hagendorn (CH)

(73) Assignee: MEDELA HOLDING AG, Baar (CH)

( * ) Notice: Subject to any disclaimer, the term of this patent is extended or adjusted under 35 U.S.C. 154(b) by 304 days.

(21) Appl. No.: 14/062,451

(22) Filed: Oct. 24, 2013

(65) Prior Publication Data
US 2014/0121593 A1 May 1, 2014

(30) Foreign Application Priority Data
Oct. 25, 2012 (CH) ..................... 02101/12

(51) Int. Cl.
*A61M 1/06* (2006.01)
*A61J 13/00* (2006.01)

(52) U.S. Cl.
CPC .............. *A61M 1/06* (2013.01); *A61M 1/064* (2014.02); *A61M 1/066* (2014.02); *A61J 13/00* (2013.01); *F04C 2270/0421* (2013.01)

(58) Field of Classification Search
CPC .......... A61M 1/007; A61M 2210/1007; A61M 1/06; A61M 1/064; A61M 1/066; A61J 13/00
USPC ..................................... 604/73–76
See application file for complete search history.

(56) References Cited

U.S. PATENT DOCUMENTS

| 4,323,067 A | 4/1982 | Adams |
| 5,049,126 A * | 9/1991 | Larsson ............... A61M 1/066 |
| | | 604/74 |
| 5,941,847 A | 8/1999 | Huber et al. |
| 7,101,350 B2 * | 9/2006 | Ytteborg ............... A61M 1/066 |
| | | 604/74 |
| 2002/0198489 A1 | 12/2002 | Silver et al. |

(Continued)

FOREIGN PATENT DOCUMENTS

| WO | WO-99/44650 A1 | 9/1999 |
| WO | WO-2011/035448 A1 | 3/2011 |

OTHER PUBLICATIONS

Search Report for Application No. CH 21012012, dated Feb. 22, 2013.

*Primary Examiner* — Bhisma Mehta
*Assistant Examiner* — William R Frehe
(74) *Attorney, Agent, or Firm* — Marshall, Gerstein & Borun LLP

(57) ABSTRACT

A breastshield unit for use in a device for expressing human breastmilk employing underpressure with a breastshield body and a media separation device which separates expressed milk from an underpressure source arranged in the breastshield body, the media separation device having a through-channel which connects first and second openings of the breastshield body. The through-channel has a through-opening, which is enlargeable when subjected to an underpressure from outside. The through-opening is formed by walls which, when subjected to an underpressure from outside, are movable away from each other, largely without stretching, in order to enlarge the through-opening. The breastshield unit permits media separation with minimal dead volume, and with optimized comfort for the mother.

17 Claims, 11 Drawing Sheets

(56) References Cited

U.S. PATENT DOCUMENTS

| | | | |
|---|---|---|---|
| 2003/0153869 A1* | 8/2003 | Ytteborg | A61M 1/064 604/74 |
| 2005/0154348 A1* | 7/2005 | Lantz | A61M 1/066 604/74 |
| 2005/0154349 A1* | 7/2005 | Renz | A61M 1/06 604/74 |
| 2006/0106334 A1* | 5/2006 | Jordan | A61M 1/0027 604/74 |
| 2008/0171970 A1* | 7/2008 | Luzbetak | A61M 1/0049 604/74 |
| 2008/0243059 A1* | 10/2008 | Yamashita | A61M 1/06 604/74 |
| 2010/0292636 A1 | 11/2010 | Renz et al. | |
| 2011/0071466 A1 | 3/2011 | Silver et al. | |
| 2012/0101432 A1 | 4/2012 | Silver | |
| 2012/0277728 A1 | 11/2012 | Weber et al. | |
| 2012/0316493 A1 | 12/2012 | Schlienger et al. | |
| 2013/0131588 A1 | 5/2013 | Silver et al. | |

* cited by examiner

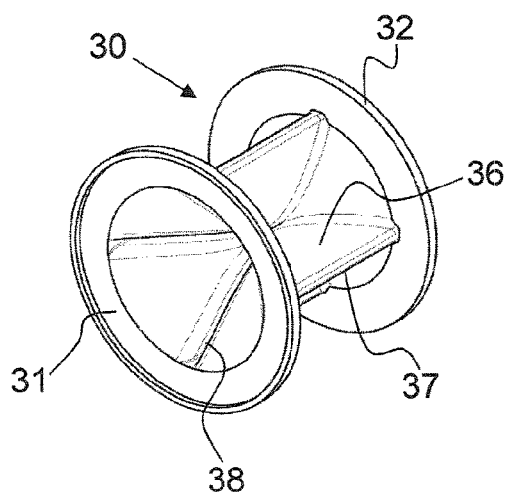
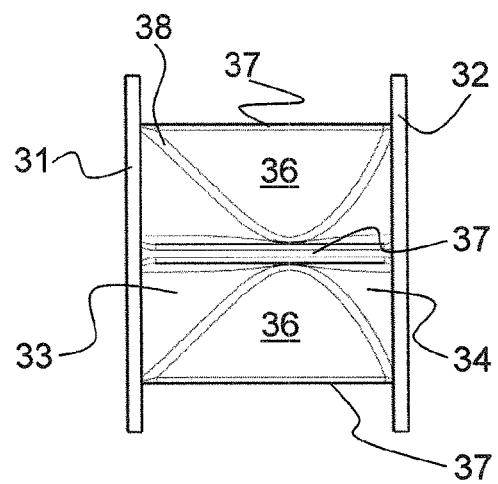
FIG. 7　　　　　　　　　　　FIG. 8
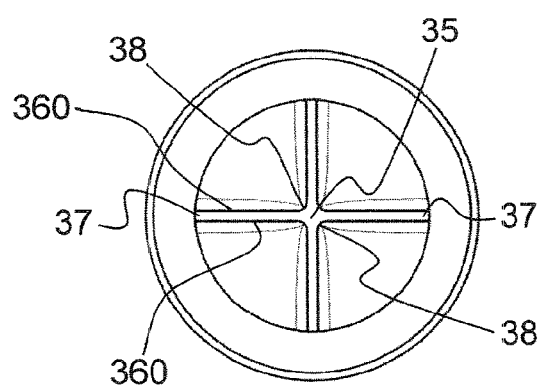
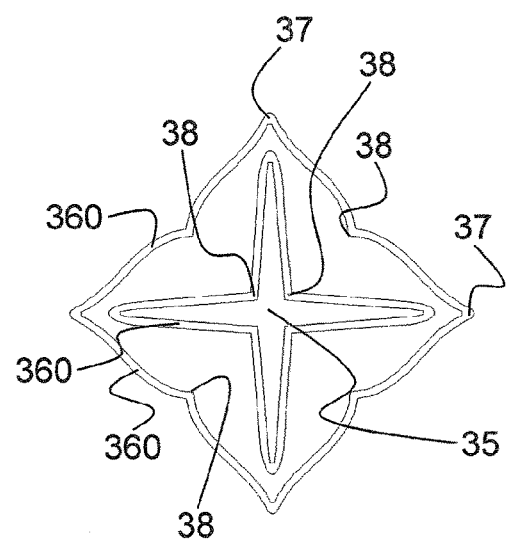
FIG. 9　　　　　　　　　　　FIG. 10

BREASTSHIELD WITH MEDIA SEPARATION

CROSS-REFERENCE TO RELATED APPLICATION

The present application claims the benefit of priority of Switzerland Application No. 02101/12, filed Oct. 25, 2012. The entire text of the priority application is incorporated herein by reference.

TECHNICAL FIELD

The present invention relates to a breastshield unit, a media separation device, and a breastshield.

PRIOR ART

Devices for expressing human breastmilk are well known. In principle, there are two different types: the first are operated manually, i.e. the underpressure needed to express milk is generated by manual actuation of the vacuum pump. In the devices of the second type, the vacuum pump is operated with an electric motor, it being possible for the vacuum pump to be connected to the power supply network and/or to be operated via a battery or another energy accumulator.

These manual or motor-operated vacuum pumps are connected to a breastshield either directly or via vacuum lines. The breastshield usually has a breastshield body for receiving the nipple. The breastshield body is usually supplemented by a funnel which bears sealingly on the mother's breast, such that a leaktight space arises around the nipple in the funnel and in the breastshield body part, in which space the underpressure generated by the vacuum pump is applied in cycles. Expressed milk flows through an opening of the breastshield into a milk collection container. This too can be done either directly or via a line. The greater the empty volume in the breastshield, the more power the breastpump has to expend in order to obtain a desired underpressure in the breastshield. This empty volume is usually called dead volume. A breastshield that minimizes the dead volume is known from WO 2011/035448. Similarly, the breastshields according to US 2012/0101432 have a small dead volume.

When expressing breastmilk, there is always the danger of milk passing into the vacuum line or even into the area of the vacuum pump and contaminating these. Therefore, in the prior art, media separation devices are known that separate the areas through which milk flows from areas in which the vacuum is applied.

Thus, U.S. Pat. No. 5,941,847 discloses a breastshield with a cylindrical membrane arranged therein, which membrane on the one hand transfers the applied vacuum to the nipple and on the other hand separates the nipple from the vacuum channel.

WO 99/44650 describes a breastshield with a soft media separation insert. This insert has a funnel-shaped part, with a cylindrical extension piece formed integrally thereon. Underpressure is applied from the outside to this extension piece, such that the latter stretches radially outwards and transfers the underpressure into its interior. The free end of the extension piece is provided with a duckbill valve, which protrudes into a milk collection container.

US 2010/0292636 discloses a manually operated breastpump with a soft breastshield insert which on the one hand is intended to enhance the mother's comfort and on the other hand likewise serves for media separation. This insert too has a funnel-shaped front part and, adjoining the latter, in this case at an angle, a substantially cylindrical extension piece which ends in a duckbill valve. The cylindrical extension piece is pressed in mechanically from the outside, as a result of which the underpressure is generated directly in the interior of the insert.

The known media separation devices offer good protection against contamination of the vacuum areas by milk. However, they reduce the pump output, since they in each case have to be stretched in order to transfer the vacuum. The media separation devices also have to be changed relatively often, since the material suffers fatigue and slackens as a result of the stretching.

DISCLOSURE OF THE INVENTION

An object of the invention is therefore to provide an improved media separation.

This object is achieved by a breastshield unit having the features of claim 1, a media separation device having the features of claim 14, and a breastshield having the features of claim 15.

The breastshield unit according to the invention for use in an appliance for expressing human breastmilk by means of underpressure has a breastshield body with a first opening for receiving a nipple of a mother's breast and with a second opening as a drain for expressed breastmilk. The breastshield unit also has a media separation device which separates expressed milk from an underpressure source. It is arranged in the breastshield body. The media separation device has a through-channel which connects the first opening of the breastshield body to the second opening of the breastshield body, wherein the through-channel has a through-opening, which is enlargeable when subjected to an underpressure from outside. The through-opening is formed by walls which, when subjected to an underpressure from outside, are movable away from each other, largely without stretching, in order to enlarge the through-opening. The breastshield unit, in particular the media separation device, is preferably dimensioned such that the media separation device surrounds the mother's breast during the intended use, i.e. for expressing breastmilk. Preferably, the above-mentioned walls surround the nipple. In the rest state, the through-opening is preferably much smaller than an average diameter of a nipple, such that the dead volume is minimized. The through-opening is preferably the smallest opening of the through-channel of the media separation device.

The media separation device acts as a pump membrane and transfers the usually cyclically applied underpressure to the nipple. Since the material of the media separation device does not have to exclusively stretch in order to transfer the vacuum, a relatively small force, and thus a relatively low pump output, is sufficient in order to transfer the vacuum into the interior of the media separation device. The material of the media separation device is barely stressed. It can be made relatively thin, which minimizes the production costs and the required pump output.

A slight stretching of the material of the media separation membrane is preferably possible. However, the enlargement of the through-opening is obtained mainly by a purely geometric shifting of the position of the walls or of the surface surrounding the through-opening. The walls preferably have a thickness of 0.5-2.0 mm.

The media separation device is arranged in that area of the breastshield in which the nipple is also received. The media separation device therefore also serves as what is called a nipple fit, i.e. the nipple is substantially enclosed by the media separation device, such that the hollow space in this area of the breastshield is minimized. In this way, the dead volume is minimized. Therefore, only a relatively small volume has to be evacuated.

A further advantage is that the cyclical movements of the walls of the media separation device massage the nipple, similarly to the palate and the tongue of a baby. This has a positive effect on the amount of milk.

Since the media separation device adapts to the anatomical circumstances of the mother's breast, the same breastshield unit can be used for different breast sizes. To ensure that the breastshield unit according to the invention can be used for all possible breast sizes, it therefore suffices to offer this breastshield unit in a relatively small number of different sizes.

In a preferred embodiment, the through-opening, and preferably also the through-channel, in a maximally opened state, i.e. usually with an underpressure applied from outside, has a non-circularly symmetrical inner cross section. However, the cross section is preferably rotationally symmetrical. This facilitates the configuration of the movable walls. An object is circularly symmetrical when a rotation through any desired angle about an axis images the object on itself. An object is rotationally symmetrical when a rotation through a defined angle about an axis images the object on itself.

In a preferred embodiment, the through-channel has an inner cross section that changes along the length of the through-channel. This also facilitates the configuration of the area around the through-opening.

Preferably, the media separation device has double walls with two individual walls, wherein the two individual walls are movable away from each other when an underpressure is applied from outside, and they thus widen the through-opening. In one embodiment, exactly one such double wall is present. Preferably, several such double walls are present, which are preferably distributed about a circumference of the media separation device. They are preferably uniformly distributed. Each double wall forms an outwardly directed web that preferably extends in a direction running parallel to the through-channel. The web forms a first edge of the two individual walls. The remaining edge of each individual wall is formed by a free edge, which is similar in shape to a parabola. This edge preferably extends from a first end of the web to a second end of the web. It is directed inwards. In the rest state, i.e. without underpressure from outside, the edges of the individual walls of a double wall preferably lie congruently on each other. In the rest state of the media separation device, these edges delimit the through-channel. When an underpressure is applied from outside, the individual walls move away from each other at the edges lying on each other, and they enlarge the cross section of the through-opening and the cross section of the rest of the through-channel.

The media separation device preferably has a main body, which is folded such that it forms, on the inside, two funnels with narrow ends inclined towards each other. A broad end of the first funnel preferably forms an inlet opening of the through-channel directed toward the breast, and a broad end of the second funnel preferably forms an outlet opening of the through-channel directed towards the milk outlet. A body of this kind can easily be produced in one piece and forms the desired complex structure with the walls that are movable away from each other.

The media separation device is preferably arranged in the breastshield with pretensioning. This can be achieved, for example, by clamping it in a twisted configuration. The opening walls thus extend in a spiral shape. They thus open and close reliably, even at low pump outputs and at relatively high pump frequencies. The pretensioning ensures in particular that the media separation membrane recovers its original shape and does not bulge out.

The media separation device preferably has, in the area of the through-opening, a cross-shaped or blossom-shaped cross section. The media separation device preferably has an approximately constant wall thickness along the length of its through-channel.

The media separation device can be formed in one piece with the breastshield body or a breastshield funnel. It can also be secured therein, e.g. injected, bonded or welded, in such a way that it cannot be detached without destruction. However, the media separation device is preferably an insert element, which is arranged releasably and removably in the breastshield body. In this way, the breastshield can be used for longer than the media separation device, or both can be cleaned separately from each other.

The media separation device is preferably made of a flexible material, in particular of silicone.

In one embodiment, the media separation device can be actuated simply by application of an underpressure. The return movement takes place automatically in each case. However, in other embodiments it is also possible to apply positive pressure, i.e. a greater pressure than atmospheric pressure, internally and/or externally to the media separation device. The positive pressure can be obtained, for example, from the exhaust of the vacuum pump. A switching valve is preferably present for this purpose.

In one embodiment, the media separation device according to the invention, for use in the above-described breastshield unit, is an insert element for arranging in a breastshield body of the breastshield unit, wherein the insert element has a through-channel which connects a first opening of the breastshield body to a second opening of the breastshield body. The through-channel has a through-opening which is enlargeable when subjected to an underpressure from outside. The through-opening is formed by walls which, when subjected to an underpressure from outside, are movable away from each other, largely without stretching, in order to enlarge the through-opening. The media separation device is preferably dimensioned such that these walls surround the nipple when the device is used as intended.

In a preferred embodiment, the inventive breastshield of an above-described breastshield unit is designed to receive and hold, when used in the manner intended, a media separation device in the form of a twisted insert element with pretensioning.

The breastshield is preferably made so small that it can also be worn in a so-called hands-free arrangement under the bra and, therefore, does not have to be held by hand.

Further embodiments are set forth in the dependent claims.

BRIEF DESCRIPTION OF THE DRAWINGS

Preferred embodiments of the invention are described below with reference to the drawings, which are provided only for explanatory purposes and are not to be interpreted as limiting the invention. In the drawings:

FIG. 7 shows a perspective view of a media separation device according to the invention in the state when not yet assembled;

FIG. 8 shows a side view of the media separation device in the state when not yet assembled, as per FIG. 7;

FIG. 9 shows a front view of the media separation device in the state when not yet assembled, as per FIG. 7;

FIG. 10 shows a schematic view of a through-opening of the media separation device as per FIG. 7 with an external underpressure;

DESCRIPTION OF PREFERRED EMBODIMENTS

Figure 3:
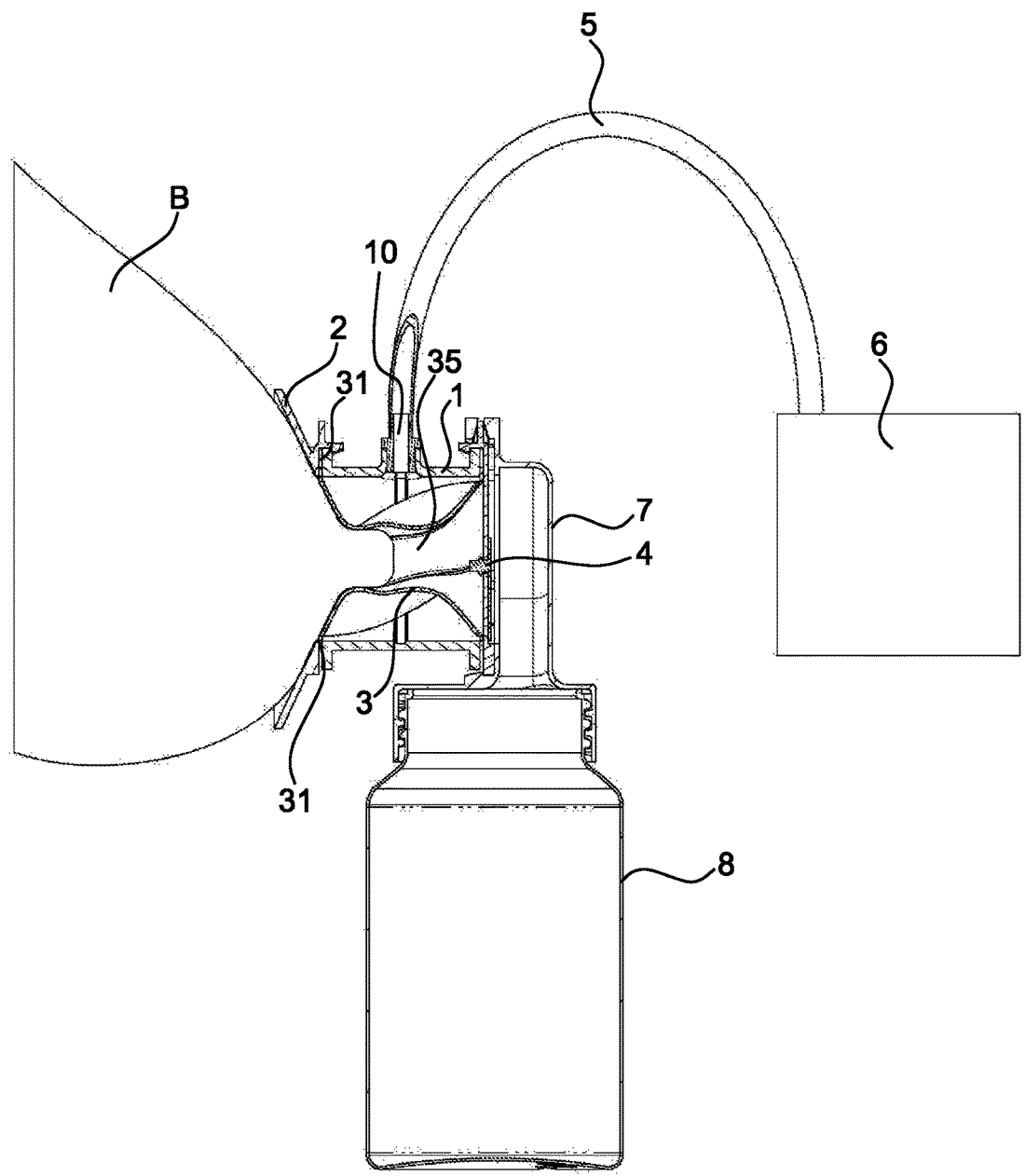
FIG. 3 shows a longitudinal section through a breastpump system with a breastshield unit according to FIG. 1.
Figure 4:
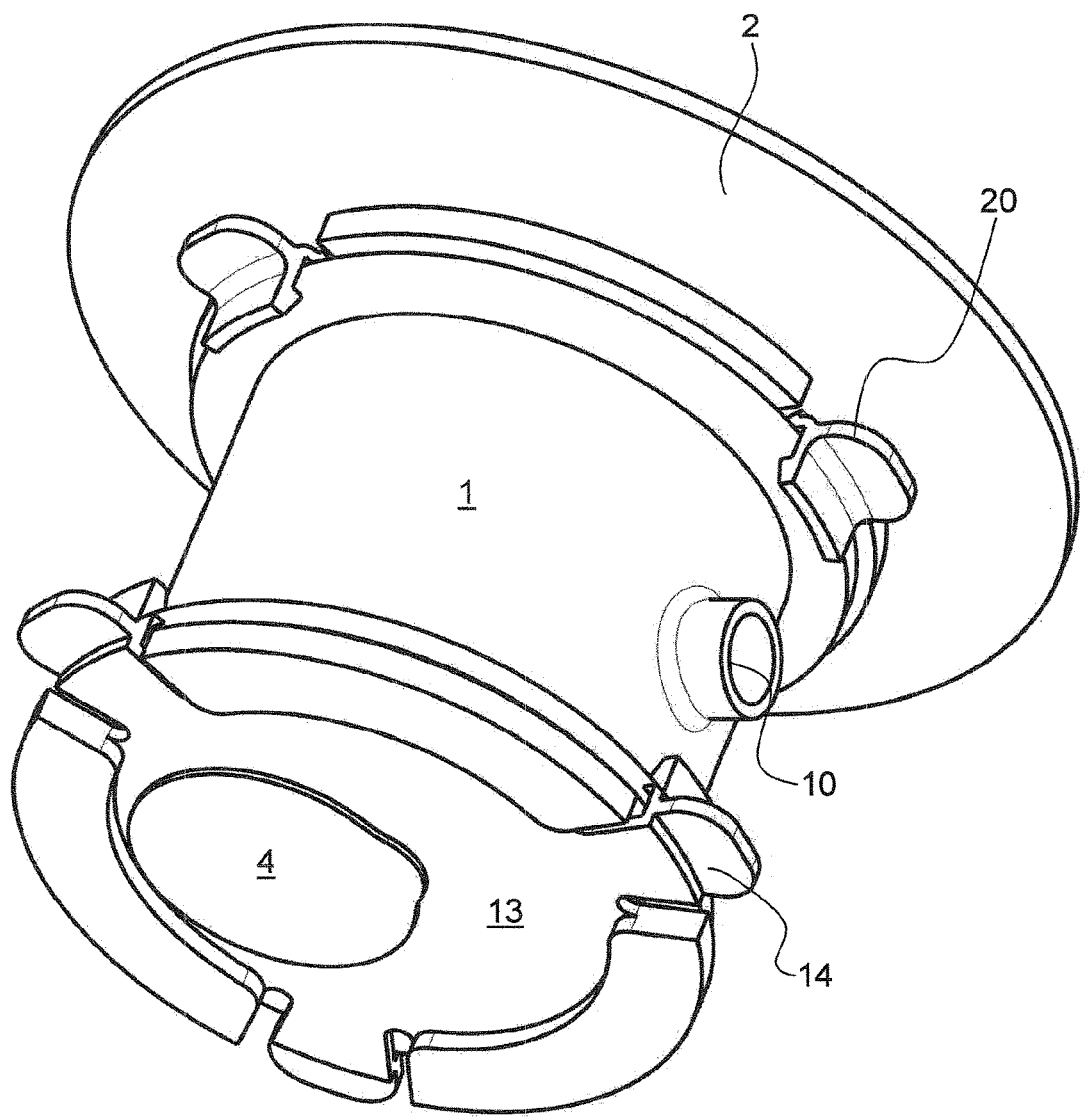
FIG. 4 shows another perspective view of the breastshield unit according to FIG. 1.

FIG. 3 shows a breastpump system with a breastshield unit according to the invention. A breastshield body 1 is provided with a breastshield funnel 2. A mother's breast B is received in this breastshield funnel 2, with the nipple of the mother's breast B protruding into the breastshield body 1. A media separation device, here a media separation membrane 3, is arranged in the breastshield body 1. It encircles at least the nipple, preferably also a part of the mother's breast B. An adapter 7 is secured on the breastshield body 1, the transition being closed by a one-way valve 4. A milk collection container 8 is secured releasably on the adapter 7. A vacuum line 5 leads from the breastshield body 1 to a vacuum pump 6.

FIGS. 1, 2, 4 and 5 show the breastshield unit with breastshield body 1, breastshield funnel 2, one-way valve 4 and media separation device 3. The breastshield body 1 is designed substantially as a hollow body. It preferably has peripheral flanges 15, 16 at both ends. It also has at least one suction connector 10 for connection to the vacuum line 5. As can be seen from FIG. 2, it preferably has one or more peripheral grooves 17 in the area of the suction connector 10, which grooves 17 distribute the applied underpressure uniformly in the space between breastshield body 1 and media separation device 3.

Figure 1:
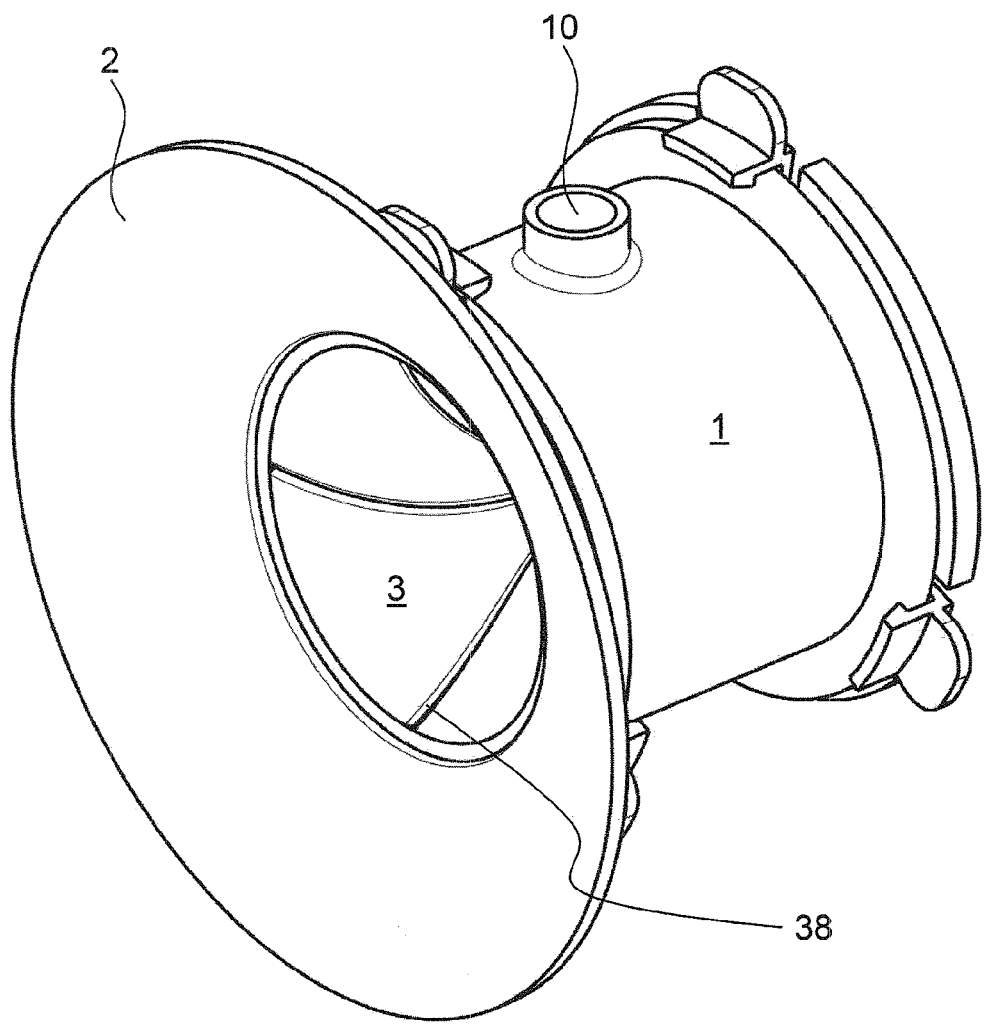
FIG. 1 shows a perspective view of a breastshield unit according to the invention in a first embodiment.
Figure 2:
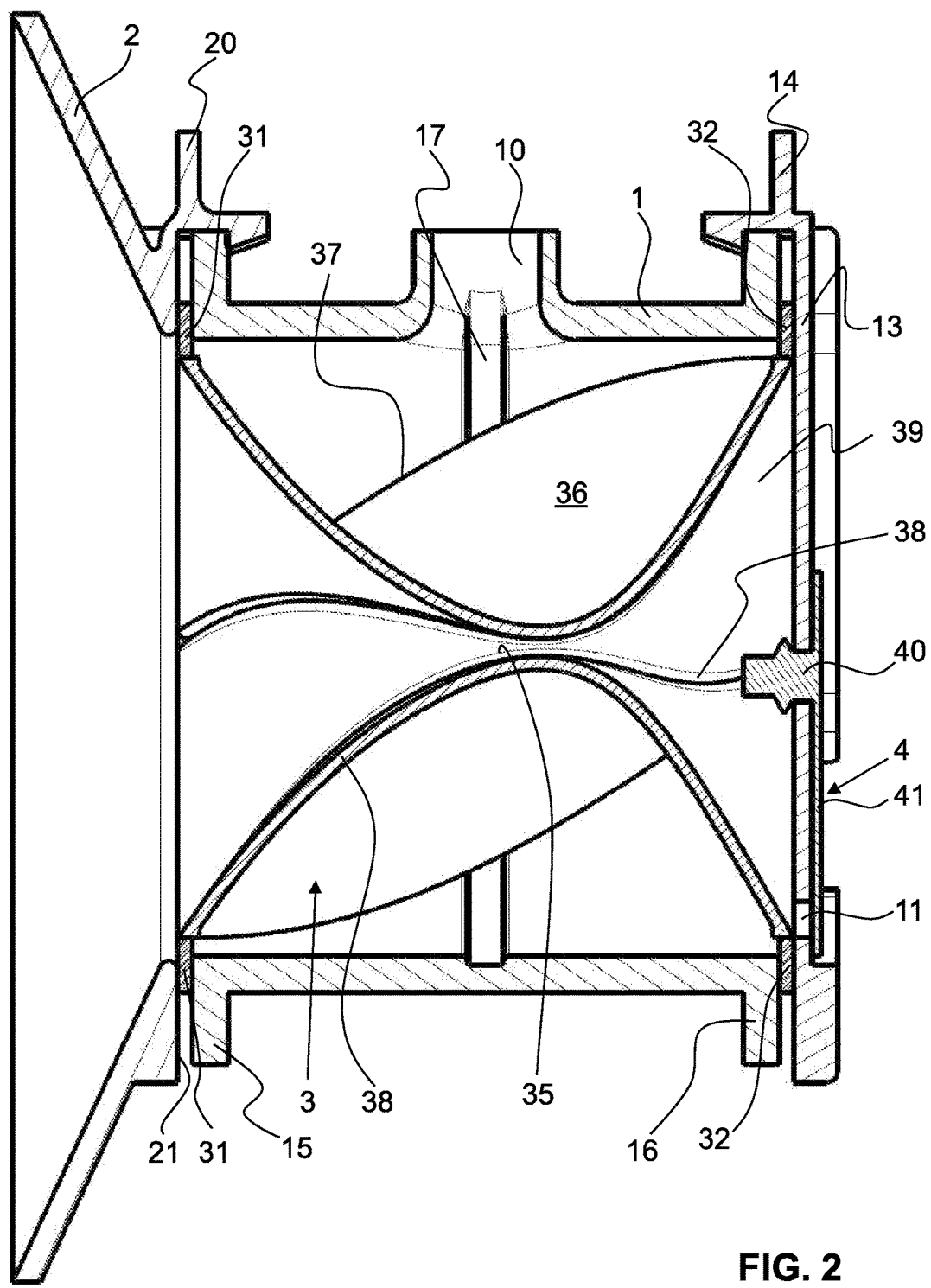
FIG. 2 shows a longitudinal section through the breastshield unit according to FIG. 1.
Figure 5:
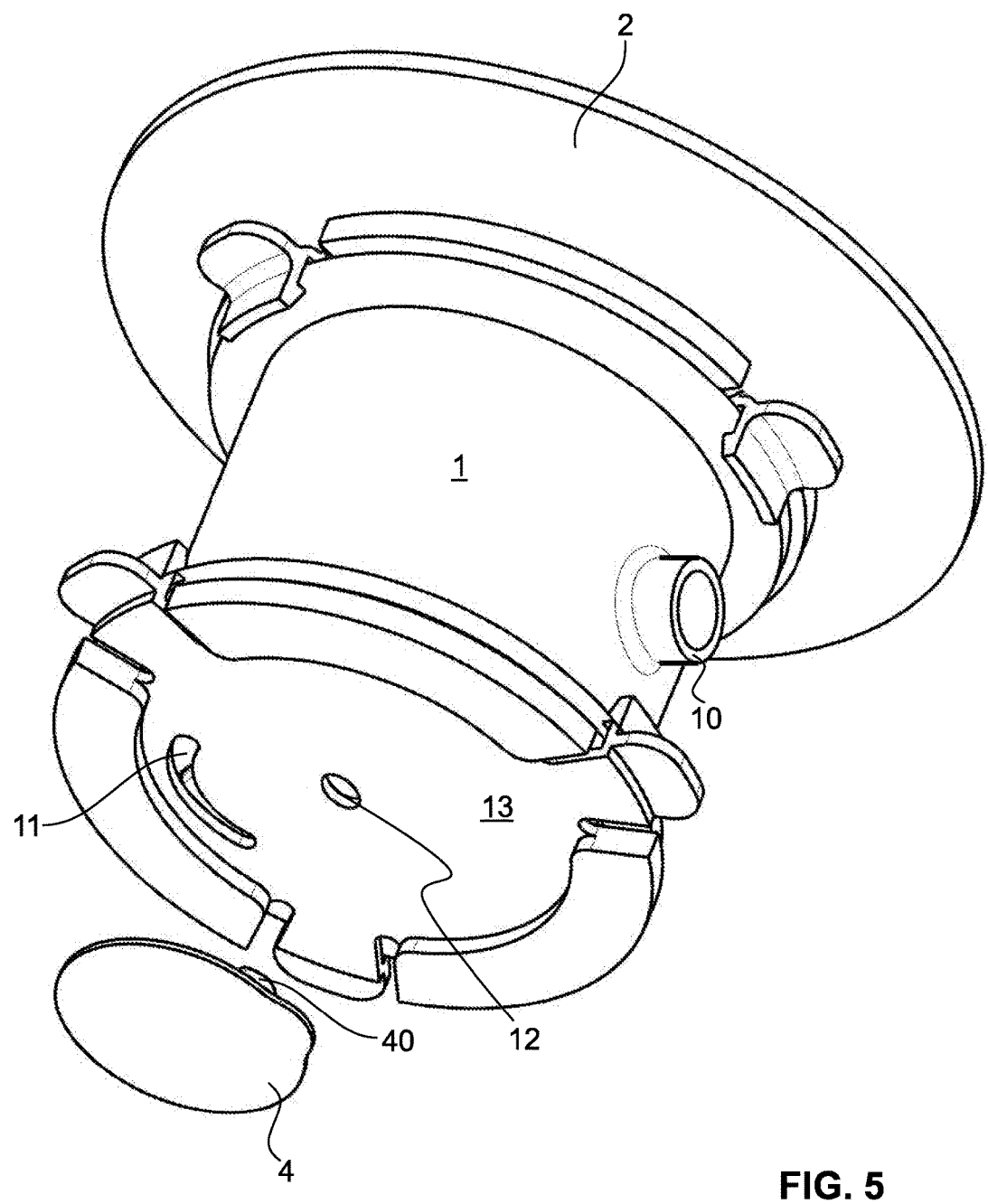
FIG. 5 shows the breastshield unit according to FIG. 4 with a one-way valve in a partially exploded view.

As can be clearly seen from FIGS. 2 and 5, the breastshield body 1 also has a separate rear wall 13 with a milk outlet opening 11. The rear wall 13 is secured releasably on the rest of the breastshield body 1 by clips 14. The milk outlet opening 11 leads via the adapter 7 to the milk collection container 8. The milk outlet opening 11 is closed by the one-way valve 4. This valve is here a flap valve 4, which has a valve flap 41 and a securing knob 40. The securing knob 40 is held in a securing opening 12 of the breastshield body 1.

Figure 6:
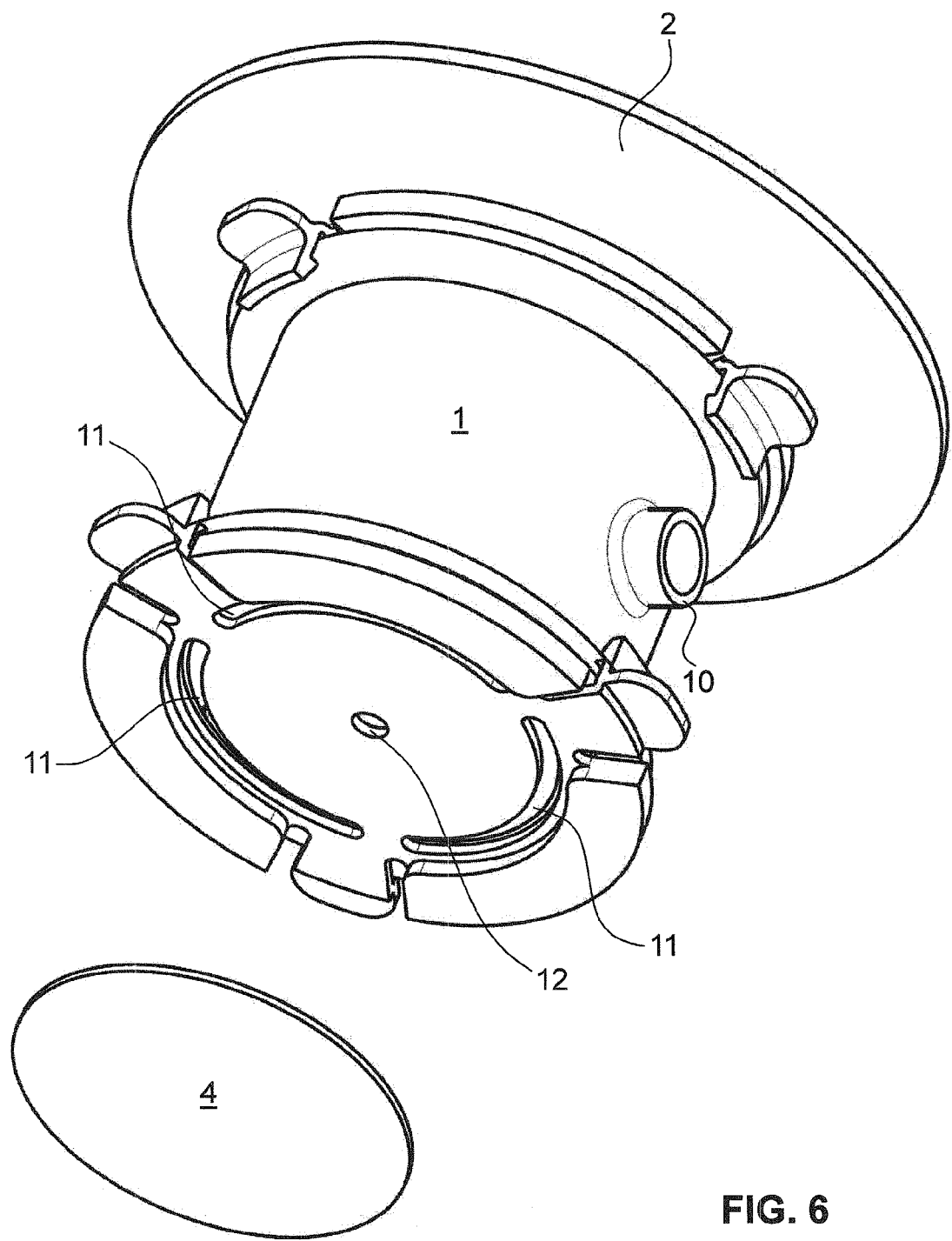
FIG. 6 shows a further embodiment of a breastpump unit according to the invention in a perspective view, with a one-way valve in a partially exploded view.

FIG. 6 shows an alternative embodiment. Here, several milk outlet openings 11 are present. The one-way valve 4 is designed accordingly.

The one-way valve 4 can also be designed differently. For example, it can be a duckbill valve.

In the example shown, the breastshield funnel 2 is secured with clips 20 on the breastshield body 1. The breastshield funnel 2 is relatively short. It preferably surrounds only a small area of the mother's breast B near the nipple. It preferably has a relatively large opening angle, preferably of between 90 and 120°.

Breastshield funnel 2 and breastshield body 1 are preferably produced from a stiff material, in particular a plastic.

The media separation device 3 is arranged in the breastshield body 1. This media separation device 3 has a main body 30 with two opposite ends. These ends are formed by a first securing flange 31 and second securing flange 32. The first securing flange 31 is clamped sealingly between a contact surface 21 of the breastshield funnel and the first flange 15 of the breastshield body 1. The second securing flange 32 of the media separation device 3 is clamped sealingly between the second flange 16 and the separate rear wall 13 of the breastshield body 1. The media separation device 3 is preferably held releasably in the breastshield body 1 such that, for the purpose of replacement or cleaning, it can be easily removed and reinstalled.

The media separation device 3 is produced at least in part from a soft, preferably elastic material. It is preferably composed of silicone. It forms a membrane. It is preferably made in one piece. As can be seen from FIG. 2, it has a through-channel which connects the opening of the breastshield funnel 2 to the milk outlet opening 11. The membrane 3 separates the opening of the breastshield funnel 2 from the suction connector 10.

It can be seen from FIG. 2 that the through-channel has a through-opening 35 which when not in use, without application of an underpressure, is practically closed or at least very small. It can be seen from FIG. 3 that, in the state of use, the nipple protrudes into the media separation device almost as far as this through-opening 35, with the nipple being enclosed by this media separation membrane 3. In FIG. 3, an underpressure is applied to the suction connector 10, as a result of which the media separation device is drawn outwards to the wall of the breastshield body 1 and the through-opening 35 is opened or enlarged. From comparing FIGS. 2 and 3, it will be clear that the diameter of the through-opening 35, without an applied underpressure, is preferably many times smaller than a diameter of a typical nipple in the unloaded state.

FIGS. 7 to 9 show a preferred embodiment of the media separation device 3 according to the invention, as used in the breastshield unit as per FIGS. 1 to 6.

It has the main body 30 with the two peripheral securing flanges 31, 32, as can be seen clearly from FIG. 7. The main body 30, which extends between the flanges 31, 32, is formed by a circumferentially closed jacket, which has the through-channel with the through-opening 35. This jacket is configured geometrically in such a way that, under the effect of an underpressure applied from outside, it can change its shape and can increase the diameter of the through-channel or of the through-opening 35 without its material having to be stretched for this purpose. The jacket is designed in such a way that it recovers its original shape when the external pressure is raised again to atmospheric pressure or back to the original pressure. The jacket is preferably elastic.

The main body 30 is basically a hollow body whose jacket wall has already been shaped in a special way at the time of production. Thus, the hollow body is shaped as two funnels 33, 34 whose narrow ends are inclined towards each other. This can be clearly seen in FIG. 8. These narrow ends preferably meet approximately at the center between the two flanges 31, 32. However, the funnels 33, 34 can also be designed with different lengths. The point at which the two narrow ends meet forms the through-opening 35. The rest of the material of the jacket between the funnels 33, 34 forms several double walls 36. Each double wall 36 has two individual walls 360, which bear against each other in the rest state of the media separation device. Each double wall 36 forms an outwardly directed web 37, which preferably extends in a direction that runs parallel to the through-channel. The outer web 37 forms a common first edge of the two individual walls 360. The remaining edge of each individual wall 360 is formed by a parabolic free edge 38. This edge 38 preferably extends from a first end of the web 37 to a second end of the web 37. It is directed inwards. The edges 38 of the individual walls 360 of a double wall 36 preferably bear congruently on each other in the rest state, i.e. without an underpressure from outside, as can be clearly seen in FIG. 9. In the rest state of the media separation device 3, these edges 38 delimit the through-channel, as can be clearly seen in FIG. 7, and form a slit.

The jacket thus has outer webs 37 and inner slits or edges 38. Four such double walls 36 are present here, such that there are four outer webs 37 and four inner slits 38 in a three-dimensional cross structure. The center of this cross structure is formed by the through-opening 35. The cross section is therefore rotationally symmetrical but not circularly symmetrical.

If an underpressure is applied from outside, the double walls 36 are drawn outwards, whereupon walls bearing on each other separate from each other at least in the area of the edges 38, and the slits open further. The through-channel and in particular the through-opening 35 are enlarged. This is shown schematically in FIG. 10. The inner lines show the area near the through-opening 35, the outer lines show the area near one of the two flanges 31, 32.

Figure 12:
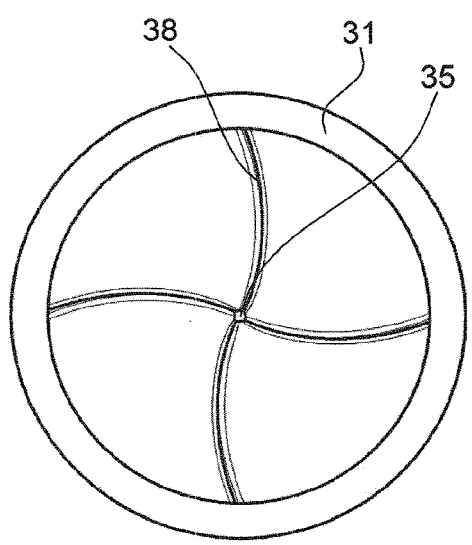
FIG. 12 shows a front view of the media separation device as per FIG. 7 in the installed state.
Figure 11:
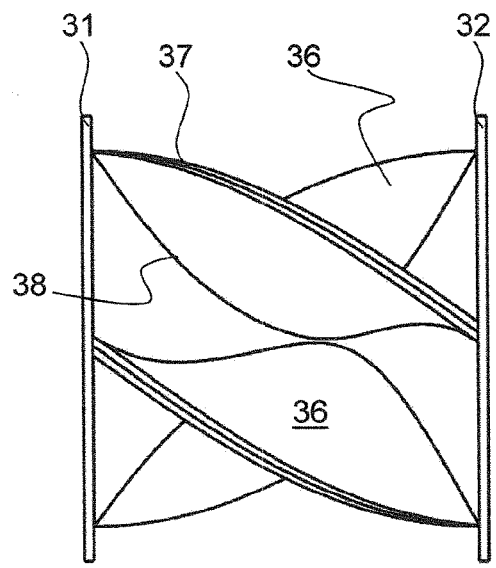
FIG. 11 shows a side view of the media separation device as per FIG. 7 in the installed state.
Figure 13:
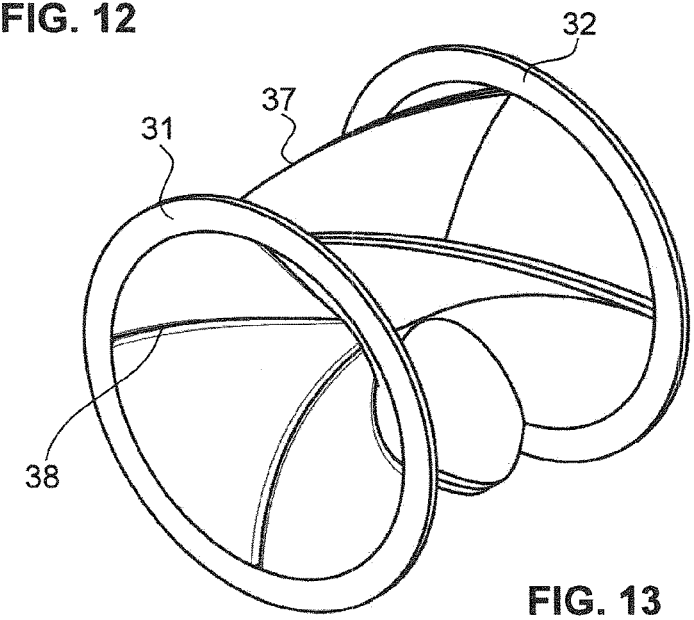
FIG. 13 shows a perspective view of the media separation device as per FIG. 7 in the installed state.

The media separation device 3 can be secured in the breastshield body 1 in the position shown in FIGS. 7 to 9. However, this membrane 3 is preferably installed in a twisted configuration. The twisting angle is preferably between 30° and 90°. For this purpose, the flanges 31, 32 are held clamped in the breastshield 1, 2 in a configuration rotated relative to each other. This rotated position is shown in FIGS. 11 and 13. In this way, the outer webs 37 and the inner edges 38 run in a spiral shape, as can be seen in FIG. 12. The three-dimensional cross structure has curved limbs.

Figure 15:
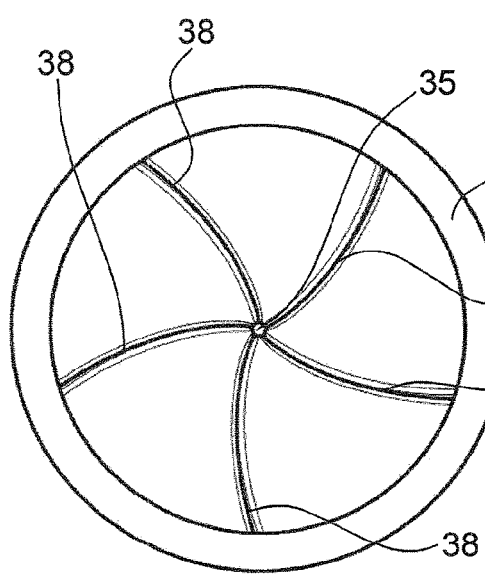
FIG. 15 shows a front view of the media separation device as per FIG. 14 in the installed state.
Figure 14:
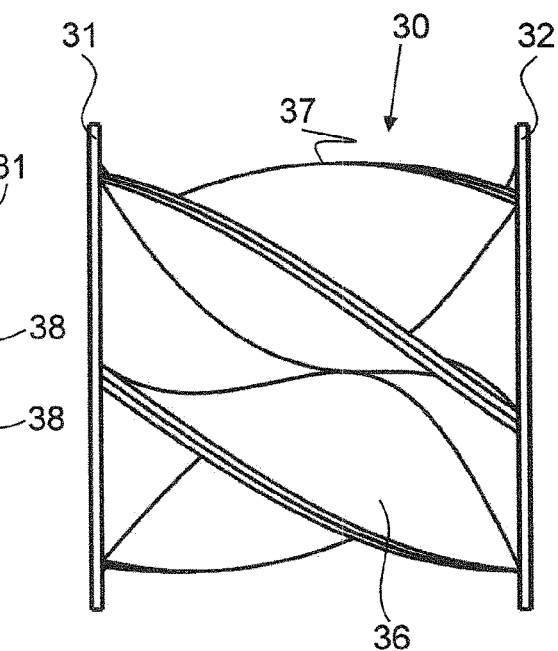
FIG. 14 shows a side view of a second embodiment of a media separation device in the installed state.
Figure 16:
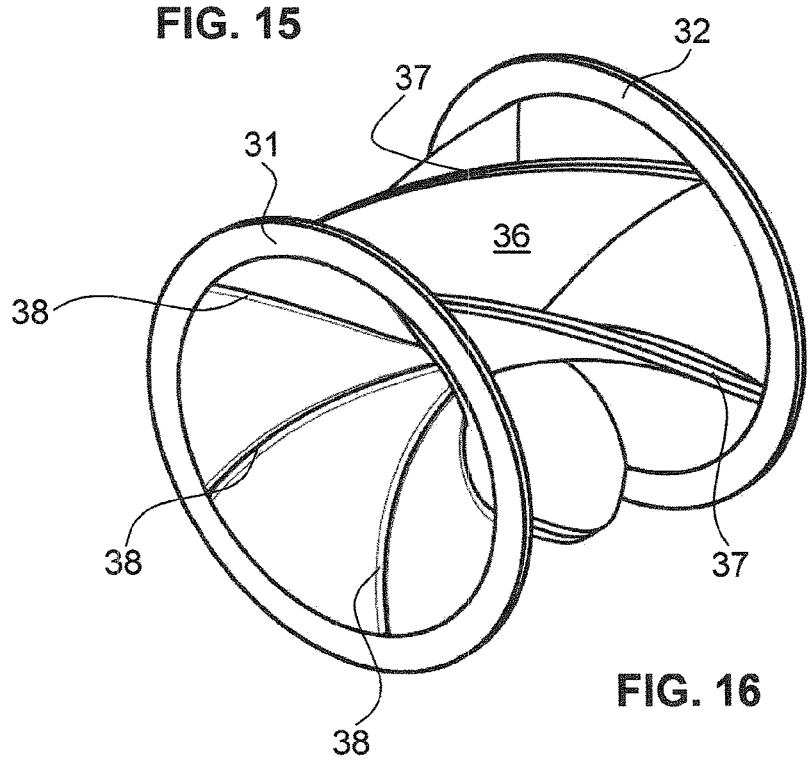
FIG. 16 shows a perspective view of the media separation device as per FIG. 14 in the installed state.

Instead of four outer webs 37 and four inner slits 38 and instead of the four-part cross structure or blossom structure, other divisions of the funnels of the jacket can be used. FIGS. 14 to 16 show a variant with five double walls 36 and therefore five webs 37 and five slits 38. They are shown already in the pretensioned position, in particular in the twisted position.

Figure 18:
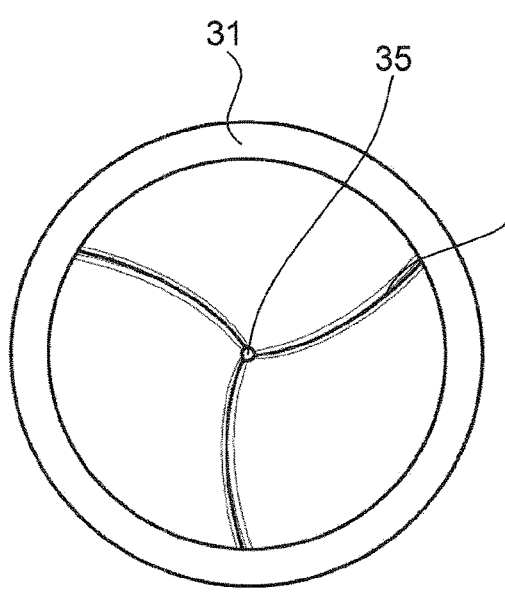
FIG. 18 shows a front view of the media separation device as per FIG. 17 in the installed state.
Figure 17:
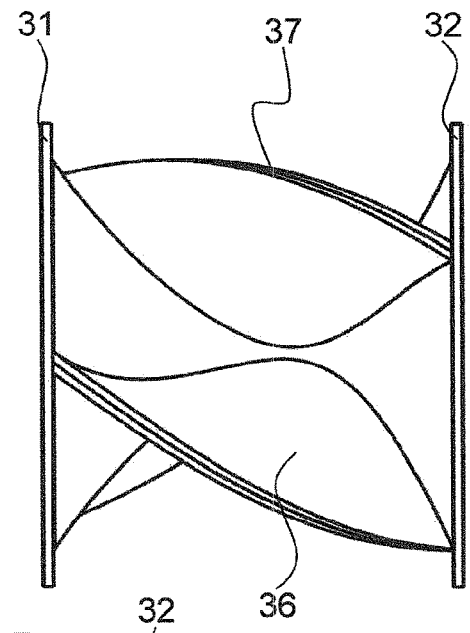
FIG. 17 shows a side view of a third embodiment of a media separation device in the installed state.
Figure 19:
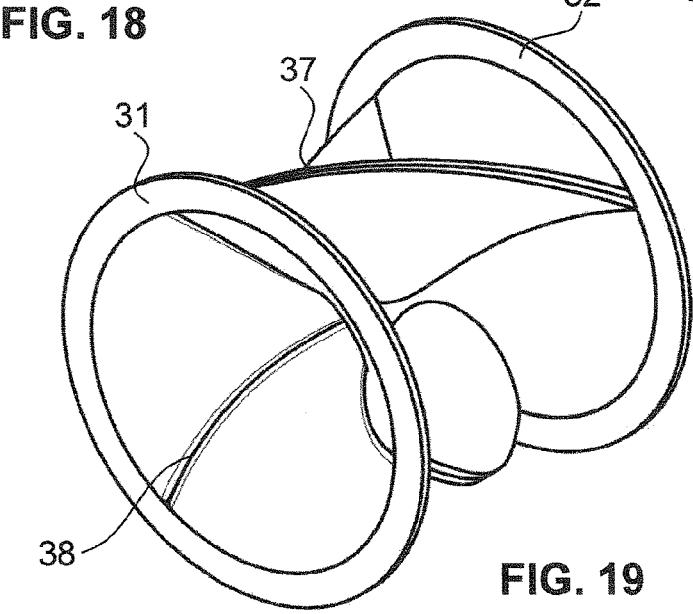
FIG. 19 shows a perspective view of the media separation device as per FIG. 17 in the installed state.

FIGS. 17 to 19 show three double walls 36 with three webs 37 and three slits 38, likewise in the pretensioned, twisted position.

Figure 20:
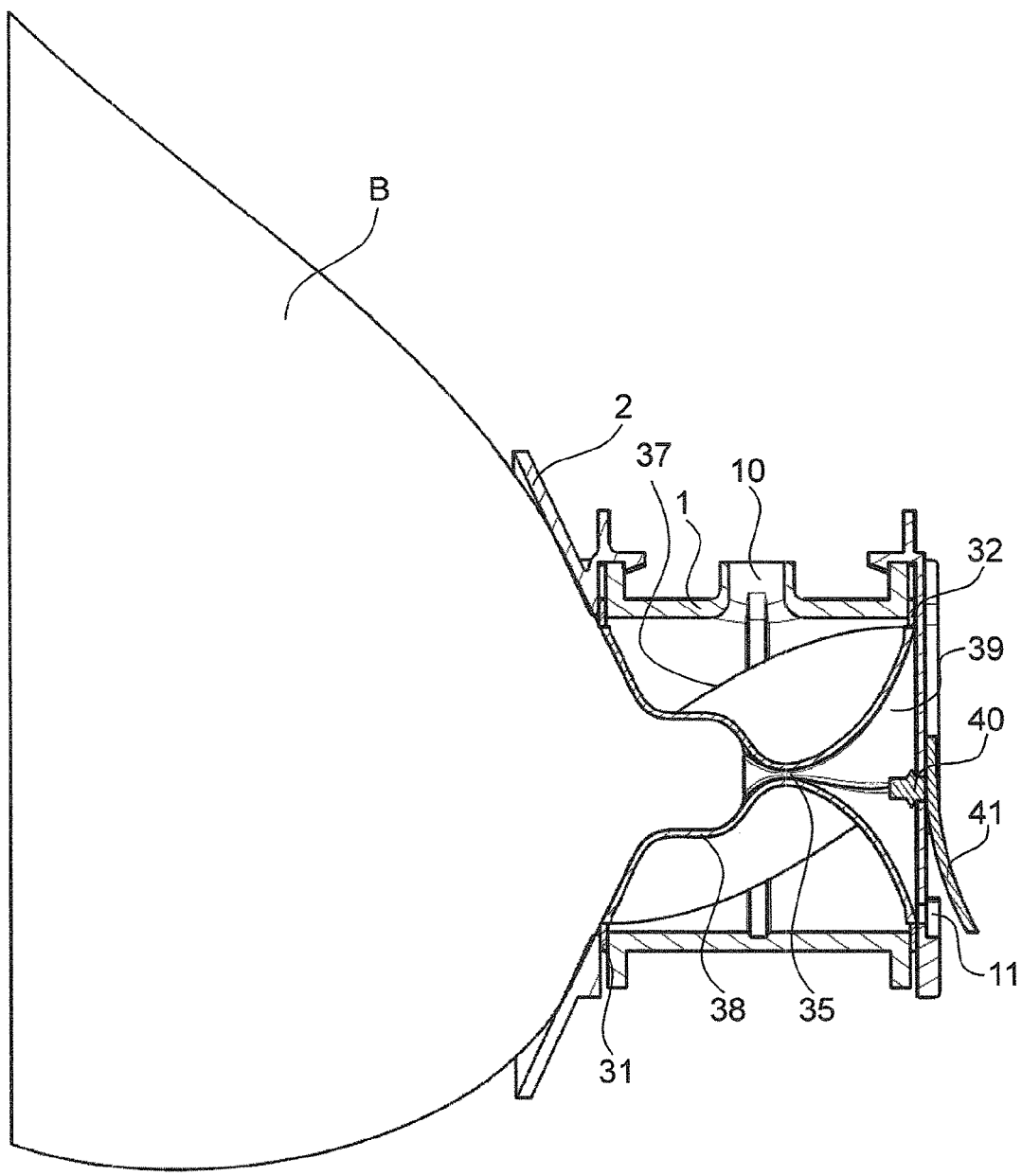
FIG. 20 shows a longitudinal section through the breastshield unit as per FIG. 1.

The mode of action of the breastshield unit according to the invention will now be explained by comparing FIGS. 3 and 20. In FIG. 3, an underpressure is applied, the double walls 36 of the membrane 3 are drawn apart and the through-opening 35 is widened. Since the mother's breast lies sealingly in the breastshield and thus sealingly closes off the interior of the media separation device 3 from the environment, an underpressure also prevails in the interior of the media separation device 3 as a result of the enlargement of the inner volume of the media separation device 3. The underpressure is thus also applied to the nipple of the mother's breast B, and milk can be aspirated into the suction chamber 39. The suction chamber 39 is formed by the interior of the media separation device 3. Because of the underpressure prevailing in this suction chamber, the valve 4 and therefore the milk outlet opening 11 is closed.

The breastpump is operated according to a suction cycle. The pressure is increased in FIG. 20, e.g. to a higher basic underpressure or even to atmospheric pressure. The media separation device recovers its original shape, i.e. the double walls 36 reform themselves again and reduce or even close the through-opening 35. In this way, the pressure in the suction chamber 39 in the interior of the media separation device 3 rises. This opens the valve 4 and the milk outlet opening 11. Milk can flow out of the suction chamber 39 into the milk collection container 8.

A number of variations of this illustrative embodiment are possible within the meaning of the invention. Thus, the breastshield can have a different design. In particular, breastshield body and breastshield funnel can be together formed in one piece. The media separation device can be arranged releasably in the breastshield in some other way. It can also be fixedly connected to the breastshield, such that separate cleaning is not possible. Moreover, the vacuum pump can be connected to the breastshield without a suction tube. The vacuum pump can be operated manually or by motor. Moreover, as is shown, the milk container can be connected to the breastshield directly or via an adapter. However, it can also be connected to the breastpump via a tube.

The breastshield unit according to the invention permits media separation with minimal dead volume, and with optimized comfort for the mother.

The invention claimed is:

1. A breastshield unit for use in a device for expressing human breastmilk by means of underpressure applied to a nipple, wherein the device comprises an underpressure source for generating the underpressure applied to the nipple, wherein the breastshield unit comprises a breastshield body with a first opening for receiving the nipple of a mother's breast, with a second opening as a drain for expressed breastmilk and with at least one third opening for connection to the underpressure source in order to apply the underpressure to the nipple, wherein the breastshield unit further comprises a media separation membrane arranged in the breastshield body, the media separation membrane being made of a flexible material and transferring the underpressure generated by the underpressure source to the nipple and the media separation membrane separating the first opening and the second opening from the at least one third opening and therefore separating the expressed breastmilk from the underpressure source and therefore protecting the underpressure source from contamination by the expressed breastmilk, wherein the media separation membrane comprises a through-channel which connects the first opening of the breastshield body to the second opening of the breastshield body, the underpressure source disposed outside of the media separation membrane, wherein the through-channel comprises a through-opening, which is enlarged when subjected to the underpressure from the underpressure source, the through-opening being formed by walls of the media separation membrane, wherein the walls, when subjected to the underpressure, are moved away from each other in order to enlarge the through-opening from an initially closed or almost closed condition, mainly by purely geometric shifting of the position of the walls, the shifting of the position of the walls being caused by the underpressure generated by the underpressure source.

2. The breastshield unit according to claim 1, wherein the through-opening, in a maximally opened state, has a non-circularly symmetrical inner cross section.

3. The breastshield unit according to claim 1, wherein the through-channel comprises an inner cross section that changes along the length of the through-channel.

4. The breastshield unit according to claim 1, wherein the media separation membrane comprises at least one double wall with two individual walls, wherein the individual walls are the walls movable away from each other.

5. The breastshield unit according to claim 4, wherein several double walls are present, which are distributed about a circumference of the media separation membrane.

6. The breastshield unit according to claim 4, wherein the individual walls are delimited by a common outer web and, moreover, by in each case a free edge, wherein the free edge has a parabolic shape.

7. The breastshield unit according to claim 1, wherein the media separation membrane comprises a main body, which is shaped such that it forms, on the inside, two funnels with narrow ends inclined towards each other.

8. The breastshield unit according to claim 7, wherein the media separation membrane includes a first securing flange at a first end of the main body and a second securing flange at a second end of the main body.

9. The breastshield unit according to claim 8, wherein the first securing flange is sealingly retained between a contact surface of the breastshield body and a first flange of the breastshield body; and the second securing flange is sealingly retained between a rear wall of the breastshield body and a second flange of the breastshield body.

10. The breastshield unit according to claim 9, wherein the rear wall of the breastshield body is releasably secured to a remainder of the breastshield body by one or more clips.

11. The breastshield unit according to claim 1, wherein the media separation membrane comprises, in the area of the through-opening, one of a cross-shaped or a blossom-shaped cross section.

12. The breastshield unit according to claim 1, wherein when the through-channel is a rest state, the breastshield unit in said rest state not being subjected to an underpressure is in the form of a double funnel, wherein a first broad end forms an inlet opening and a second broad end forms an outlet opening, and wherein the double funnel between these two ends tapers towards the through-opening.

13. The breastshield unit according to claim 1, wherein the media separation membrane is arranged with pretensioning in the breastshield body.

14. The breastshield unit according to claim 1, wherein the media separation membrane is arranged in a twisted configuration in the breastshield body.

15. The breastshield unit according to claim 1, wherein the media separation membrane is an insert element, which is arranged detachably and removably in the breastshield body.

16. A media separation membrane of a breastshield unit for use in a device for expressing human breastmilk by means of underpressure applied to a nipple,
wherein the device comprises an underpressure source for generating the underpressure applied to the nipple, the underpressure source disposed outside of the media separation membrane,
wherein the breastshield unit comprises a breastshield body with a first opening for receiving the nipple of a mother's breast, with a second opening as a drain for expressed breastmilk and with at least one third opening for connection to the underpressure source in order to apply the underpressure to the nipple,
wherein the media separation membrane is an insert element for arranging in the breastshield body, the media separation membrane being made of a flexible material and transferring the underpressure generated by the underpressure source to the nipple and the media separation membrane separating the first opening and the second opening from the at least one third opening and therefore separating the expressed breastmilk from the underpressure source and therefore protecting the underpressure source from contamination by the expressed breastmilk,
wherein the media separation membrane comprises a through-channel which connects the first opening of the breastshield body to the second opening of the breastshield body, wherein the through-channel comprises a through-opening, which is enlarged when subjected to the underpressure from the underpressure source, the through-opening being formed by walls of the media separation membrane which, when subjected to the underpressure, are moved, from an initial closed or almost closed condition, away from each other in order to enlarge the through-opening, mainly by purely geometric shifting of the position of the walls, the shifting of the position of the walls being caused by the underpressure generated by the underpressure source.

17. A breastshield of a breastshield unit for use in a device for expressing human breastmilk by means of underpressure applied to a nipple, wherein the device comprises an underpressure source for generating the underpressure applied to the nipple,
wherein the breastshield comprises a breastshield body with a first opening for receiving the nipple of a mother's breast, with a second opening as a drain for expressed breastmilk and with at least one third opening for connection to the underpressure source in order to apply the underpressure to the nipple, and
wherein the breastshield is designed to receive and releasably and removably hold a media separation membrane being made of a flexible material and in the form of a twisted insert element with pretensioning, the media separation membrane transferring the underpressure generated by the underpressure source, which under pressure source is disposed outside the media separation membrane, to the nipple and the media separation membrane separating the first opening and the second opening from the at least one third opening and therefore separating the expressed breastmilk from the underpressure source and therefore protecting the underpressure source from contamination by the expressed breastmilk, wherein the media separation membrane comprises a through-channel which connects the first opening of the breastshield body to the second opening of the breastshield body, wherein the through-channel comprises a through-opening, which is enlarged when subjected to the underpressure from the underpressure source, the through-opening being formed by walls of the media separation membrane which, when subjected to the underpressure, are moved, from an initial closed or almost closed condition, away from each other in order to enlarge the through-opening, mainly by purely geometric shifting of the position of the walls, the shifting of the position of the walls being caused by the underpressure generated by the underpressure source.

* * * * *